United States Patent [19]

Kramer et al.

[11] Patent Number: 5,519,074
[45] Date of Patent: May 21, 1996

[54] COMPLEXES OF MORPHOLINE DERIVATIVES WITH KETO-ACIDS AS CORROSION INHIBITORS

[75] Inventors: Andreas Kramer, Düdingen, Switzerland; Adalbert Braig, Binzen, Germany

[73] Assignee: Ciba-Geigy Corporation, Tarrytown, N.Y.

[21] Appl. No.: 371,632

[22] Filed: Jan. 12, 1995

[30] Foreign Application Priority Data

Jan. 18, 1994 [CH] Switzerland .................. 149/94

[51] Int. Cl.⁶ .................................................. C08K 5/34
[52] U.S. Cl. .................. 524/99; 524/104; 524/288; 524/289; 252/391; 252/392; 252/396; 544/162; 544/170; 544/171; 544/173
[58] Field of Search ............... 524/99, 104, 289, 524/288, 98; 252/391, 392, 396; 544/162, 170, 172, 173

[56] References Cited

U.S. PATENT DOCUMENTS

| | | | |
|---|---|---|---|
| 4,366,076 | 12/1982 | Clark | 252/34 |
| 4,909,987 | 3/1990 | Penninger et al. | 422/17 |
| 5,128,396 | 7/1992 | O'Neil et al. | 524/288 |

FOREIGN PATENT DOCUMENTS

| | | |
|---|---|---|
| 0041927 | 6/1981 | European Pat. Off. . |
| 0144663 | 6/1985 | European Pat. Off. . |
| 0300325 | 1/1989 | European Pat. Off. . |
| 0412933 | 2/1991 | European Pat. Off. . |
| 0496555 | 7/1992 | European Pat. Off. . |

OTHER PUBLICATIONS

Houben–Weyl, Methoden der Organischen Chemie, Band VII, pp. 381–382 (1952).
Houben–Weyl, Methoden der Organischen Chemie, Band E5, pp. 398–399 (1985).
Houben–Weyl, Methoden der Organischen Chemie, Band XI/1 p. 815 (1957).
Indian Journal of Tech. vol. 8, #3 (Mar. 1970) pp. 98–100 R. Natarajan et al.

*Primary Examiner*—Jeffrey T. Smith
*Attorney, Agent, or Firm*—Michele A. Kovaleski

[57] ABSTRACT

The invention relates to crystalline complex compounds of formula I

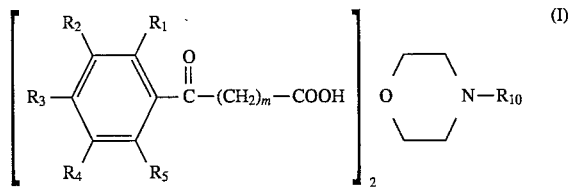

wherein the general symbols are as defined in claim 1, as corrosion inhibitors in coating compositions for protecting metallic surfaces.

17 Claims, 2 Drawing Sheets

COMPLEXES OF MORPHOLINE DERIVATIVES WITH KETO-ACIDS AS CORROSION INHIBITORS

The present invention relates to complexes of morpholine derivatives with keto-acids, to coating compositions comprising an organic film-forming binder, preferably a paint system and the novel corrosion inhibitors, as well as to the use thereof in coating compositions for protecting metallic surfaces.

BACKGROUND OF THE INVENTION

The use of alkali metal, ammonium and amine salts of keto-acids as corrosion inhibitors in aqueous systems is known and disclosed, inter alia, in U.S. Pat. No. 4,909,987, U.S. Pat. No. 5,128,396 or EP-A-496 555.

In EP-A-300 325, Example 7, it is taught that the reaction of one equivalent of 3-benzoylpropionic acid with one equivalent of morpholine in ethanol yields a crystalline salt composed, as expected, of one part of acid and one part of base.

It has now been found that the reaction of a keto-acid with a morpholine derivative, without a solvent, or in the presence of an aprotic solvent, yields crystalline complexes composed of two parts of acid and only one pan of base. These crystalline complex compounds are very particularly suitable for use as corrosion inhibitors in coating compositions for protecting metallic surfaces and also for pretreating metallic substrates. The crystalline complex compounds do not lead to a reaction with the paint system, especially an aqueous paint system, and are distinguished by excellent storage stability in coating compositions. They are likewise suitable for both temporary as well as permanent rust protection. These paint systems also exhibit excellent wet bonding strength.

DESCRIPTION OF THE INVENTION

Figure 1:
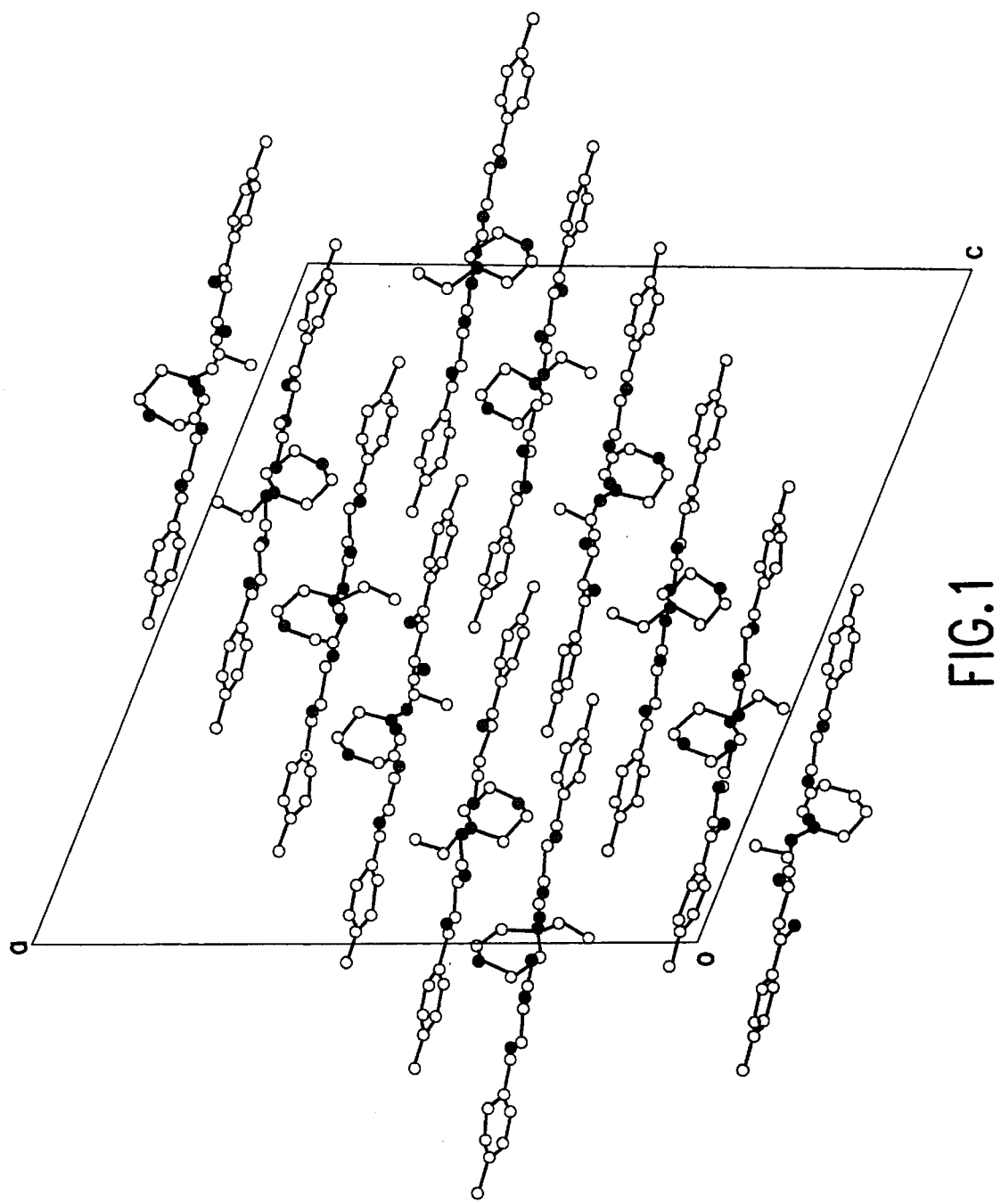
FIG. 1 illustrates the crystal packing of the complex compound 101 (Example 1), as determined by X-ray structural analysis.

Accordingly, the invention relates to crystalline complex compounds of formula I

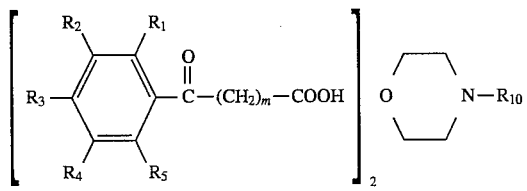

wherein $R_1$, $R_2$, $R_3$, $R_4$ and $R_5$ are each independently of one another hydrogen, halogen, nitro, cyano, $CF_3$, $C_1$–$C_{15}$alkyl, $C_5$–$C_{12}$cycloalkyl, $C_2$–$C_{15}$alkenyl, $C_1$–$C_{12}$haloalkyl, $C_1$–$C_{12}$alkoxy, $C_1$–$C_{12}$alkylthio, unsubstituted or $C_1$–$C_4$alkyl-substituted $C_6$–$C_{10}$aryl; unsubstituted or $C_1$–$C_4$alkyl-substituted $C_6$–$C_{10}$aryloxy; unsubstituted $C_7$–$C_{12}$arylalkyl or $C_7$–$C_{12}$arylalkyl which is substituted in the aryl moiety by 1 to 3 $C_1$–$C_4$alkyl groups;

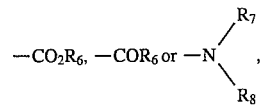

with the proviso that at least one of $R_1$ to $R_5$ is hydrogen, halogen or $C_1$–$C_{15}$alkyl; and each pair of substituents $R_1$ and $R_2$, $R_2$ and $R_3$, $R_3$ and $R_4$ or $R_4$ and $R_5$, together with the linking carbon atom, form a benzene or cyclohexenyl ring, $R_6$ is $C_1$–$C_{20}$alkyl, $C_2$–$C_{20}$alkyl which is interrupted by oxygen, sulfur or

unsubstituted $C_7$–$C_{12}$arylalkyl or $C_7$–$C_{12}$arylalkyl which is substituted in the aryl moiety by 1 to 3 $C_1$–$C_4$alkyl groups;

$R_7$ and $R_8$ are each independently of the other hydrogen, $C_1$–$C_{24}$alkyl or $C_2$–$C_{24}$alkyl which is interrupted by oxygen, sulfur or

$R_9$ is hydrogen or $C_1$–$C_8$alkyl, $R_{10}$ is $C_1$–$C_{15}$alkyl, $C_2$–$C_{20}$alkyl which is interrupted by oxygen, sulfur or

$C_5$–$C_{12}$cycloalkyl, $C_2$–$C_{15}$alkenyl, $C_1$–$C_{12}$alkoxy, $C_1$–$C_{12}$alkylthio, unsubstituted or $C_1$–$C_4$alkyl-substituted $C_6$–$C_{10}$aryl; unsubstituted or $C_1$–$C_4$alkyl-substituted $C_6$–$C_{10}$aryloxy; unsubstituted $C_7$–$C_{12}$arylalkyl or $C_7$–$C_{12}$arylalkyl which is substituted in the aryl moiety by 1 to 3 $C_1$–$C_4$alkyl groups; and m is an integer from 2 to 5.

Halogen will typically be taken to mean fluoro, chloro, bromo or iodo. Preferred halogen substituents are fluoro, chloro or bromo. Chloro or bromo is particularly preferred.

Alkyl containing up to 24 carbon atoms is a branched or unbranched radical, typically including methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3, 3,5,5-hexamethylhexyl, tridecyl, tetradecyl, pentadecyl, hexadecyl, heptadecyl, octadecyl, eicosyl or docosyl. Preferably alkyl contains 1 to 12, more particularly 1 to 8, carbon atoms. The preferred meaning of $R_3$ is $C_1$–$C_4$alkyl, more particularly methyl. A preferred meaning of $R_{10}$ is $C_1$–$C_4$alkyl, more particularly ethyl.

$C_5$–$C_{12}$Cycloalkyl is typically cyclopentyl, cyclohexyl, cycloheptyl, cyclooctyl, cyclodecyl or cyclododecyl. Cyclohexyl is preferred.

Alkenyl of 2 to 15 carbon atoms is a branched or unbranched radical such as vinyl, 2-propenyl (allyl), 2-butenyl, 3-butenyl, isobutenyl, n-2,4-pentadienyl, 3-methyl-2-butenyl, n-2-octenyl, n-2-dodecenyl or isododecenyl. Preferably alkenyl contains 3 to 12, more particularly 3 to 8, e.g. 3 to 6, most preferably, 3 to 4 carbon atoms.

Haloalkyl containing up to 12 carbon atoms is a branched or unbranched radical such as chloromethyl, bromoethyl, fluoropropyl, chloropentyl, chlorohexyl, chlorooctyl, chlorodecyl or chlorododecyl. Haloalkyl preferably contains 3 to 8, more particularly 3 to 6, carbon atoms.

Alkoxy containing up to 12 carbon atoms is a branched or unbranched radical such as methoxy, ethoxy, propoxy, isopropoxy, n-butoxy, isobutoxy, pentoxy, isopentoxy, hexoxy, heptoxy, octoxy or decyloxy. Preferably alkoxy contains 1 to to 8, more particularly 1 to 4, carbon atoms.

Alkylthio containing up to 12 carbon atoms is a branched or unbranched radical such as methylthio, ethylthio, propylthio, isopropylthio, n-butylthio, isobutylthio, pentylthio, isopentylthio, hexylthio, heptylthio, octylthio, decylthio or dodecylthio. Preferably alkylthio contains 1 to 8, more particularly 1 to 4, carbon atoms.

Unsubstituted or $C_1$–$C_4$alkyl-substituted $C_6$–$C_{10}$aryl which preferably carries 1 to 3, more particularly 1 or 2, alkyl groups, is typically phenyl, naphthyl, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl, 2,6-diethylphenyl, 2-methylnaphthyl, 1-methylnaphthyl, 4-methylnaphthyl, 2-ethylnaphthyl or 2,6-diethylnaphthyl.

Unsubstituted or $C_1$–$C_4$alkyl-substituted $C_6$–$C_{10}$aryloxy which carries preferably 1 to 3, more particularly 1 or 2, alkyl groups, is typically phenoxy, naphthoxy, o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy, 2,6-diethylphenoxy, 2-methylnaphthoxy, 1-methylnaphthoxy, 4-methylnaphthoxy, 2-ethylnaphthoxy or 2,6-diethylnaphthoxy.

$C_7$–$C_{12}$Arylalkyl which is unsubstituted or substituted in the aryl moiety by 1 to 3 $C_1$–$C_4$ alkyl groups is typically phenyl-$C_1$–$C_6$alkyl or naphthyl-$C_1$–$C_2$alkyl, e.g. benzyl, 4-methylbenzyl, 4-tert-butylbenzyl, 2,4-dimethylbenzyl, α-methylbenzyl, α,α-dimethylbenzyl, 2-phenylethyl, 2-naphthylmethyl, 1-naphthylmethyl, 1-naphthylethyl or 2-naphthylethyl. Benzyl is preferred.

Alkyl containing 2 to 24 carbon atoms which is interrupted by oxygen, sulfur or

may typically be $CH_3$—O—$CH_2$—, $CH_3$—S—$CH_2$—, $CH_3$—NH—$CH_2$—, $CH_3$—N($CH_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—.

Crystalline complex compounds of formula I, wherein at least two of $R_1$ to $R_5$ are hydrogen, are preferred.

m in formula I is preferably 2 to 4, most preferably 2.

Particularly preferred crystalline complex compounds of formula I, are those wherein $R_1$ is hydrogen, $R_2$, $R_3$, $R_4$ and $R_5$ are each independently of one another hydrogen, chloro, bromo, nitro, cyano, $CF_3$, $C_1$–$C_8$alkyl, $C_5$–$C_7$cycloalkyl, $C_3$–$C_8$alkenyl, $C_1$–$C_8$alkoxy, $C_1$–$C_8$alkylthio, phenyl, phenoxy, benzyl,

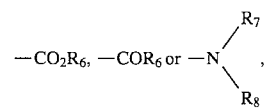

$R_6$ is $C_1$–$C_{12}$alkyl, $C_2$–$C_{12}$alkyl which is interrupted by oxygen; or benzyl, and $R_7$ and $R_8$ are each independently of the other hydrogen, $C_1$–$C_8$alkyl or $C_2$–$C_{12}$alkyl which is interrupted by oxygen.

Also particularly preferred are crystalline complex compounds of formula I, wherein $R_{10}$ is $C_1C_8$alkyl, $C_3$–$C_{12}$alkyl which is interrupted by oxygen or sulfur; $C_5$–$C_7$cycloalkyl, $C_3$–$C_8$alkenyl, $C_1$–$C_8$alkoxy, $C_1C_8$alkylthio, phenyl, phenoxy or benzyl.

Further particularly preferred crystalline complex compounds of formula I are those wherein $R_1$, $R_2$ and $R_4$ are hydrogen, $R_3$ and $R_5$ are each independently of the other hydrogen, chloro, bromo, $CF_3$, $C_1$–$C_8$alkyl, cyclohexyl, $C_1$–$C_8$alkoxy, phenyl,

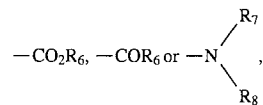

$R_6$ is $C_1$–$C_8$alkyl, $R_7$ and $R_8$ are each independently of the other hydrogen or $C_1$–$C_8$alkyl, $R_{10}$ is $C_1$–$C_8$alkyl, cyclohexyl, phenyl or benzyl, and m is an integer from 2 to 4.

Particularly interesting crystalline complex compounds of formula I are those wherein $R_1$, $R_2$, $R_4$ and $R_5$ are hydrogen, and m is 2.

Crystalline complex compounds of formula I, wherein $R_{10}$ is $C_1$–$C_4$alkyl, merit very special interest.

Crystalline complex compounds of formula I which also merit interest are those wherein $R_1$, $R_2$, $R_4$ and $R_5$ are hydrogen, $R_3$ is hydrogen, $C_1$–$C_4$alkyl, phenyl or chloro, $R_{10}$ is $C_1$–$C_4$alkyl, and m is 2.

The crystalline 2:1 complex of 3-(4-methylbenzoyl)propionic acid with N-ethylmorpholine [compound (101)] is very particularly preferred.

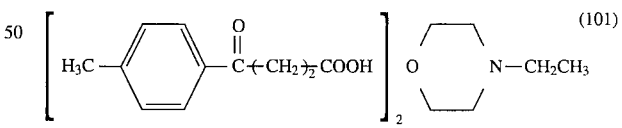

Figure 2:
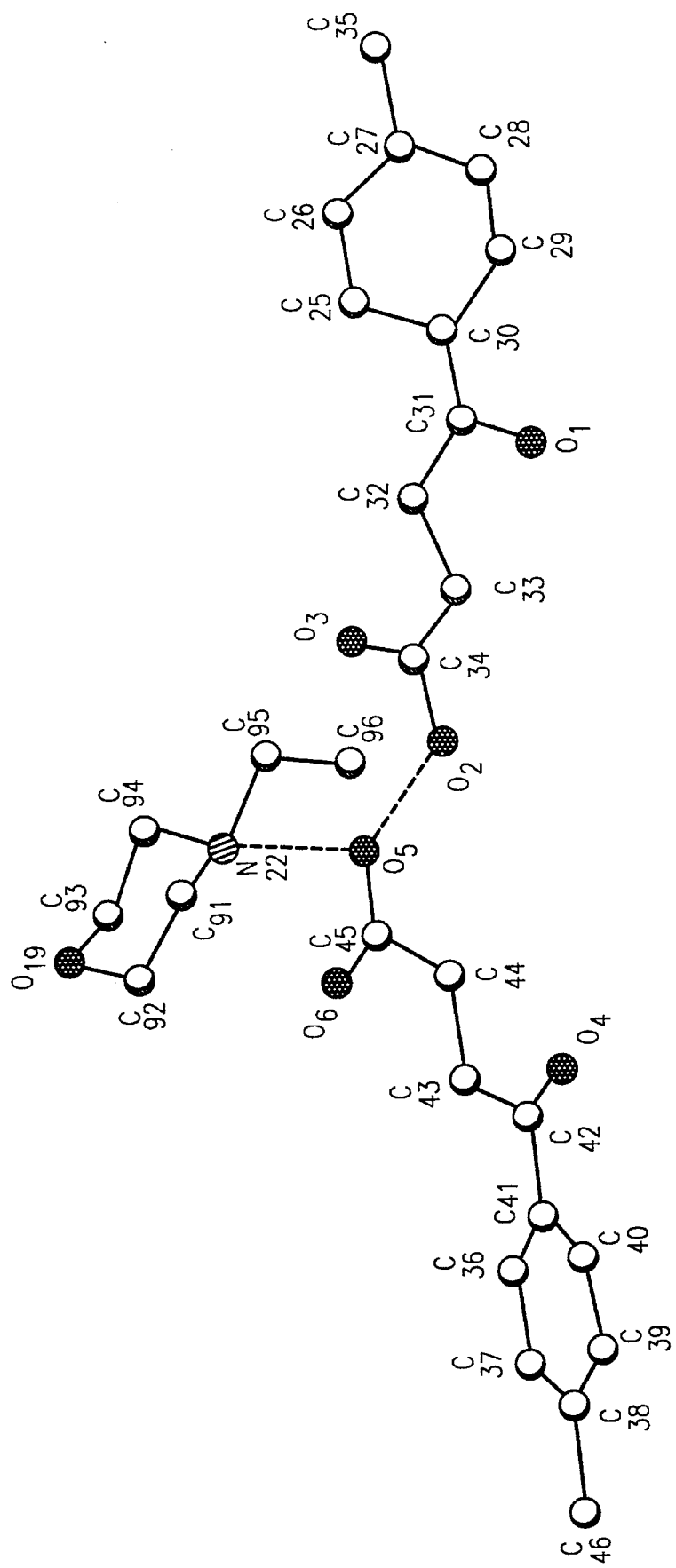
FIG. 2 sets forth the numbering of the atoms in the complex compound 101 (Example 1).

An X-ray structural analysis has been made of this complex compound (101) (Example 1). FIG. 1 illustrates the crystal packing and FIG. 2 the numbering of the atoms in the complex compound (101). The experimental crystal data are given in Example 1.

The average bond lengths in Angstrom are given in Table 1.

TABLE 1

| \multicolumn{6}{c}{Average bond lengths in Å} |
|---|---|---|---|---|---|
| O (1) | C (31) | 1.255 Å | O (2) | C (34) | 1.332 Å |
| O (3) | C (34) | 1.252 Å | O (4) | C (42) | 1.244 Å |

TABLE 1-continued

Average bond lengths in Å

| | | | | | |
|---|---|---|---|---|---|
| O (5) | C (45) | 1.251 Å | O (6) | C (45) | 1.260 Å |
| O (19) | C (92) | 1.440 Å | O (19) | C (93) | 1.471 Å |
| N (22) | C (91) | 1.547 Å | N (22) | C (94) | 1.501 Å |
| N (22) | C (95) | 1.561 Å | C (25) | C (26) | 1.420 Å |
| C (25) | C (30) | 1.412 Å | C (26) | C (27) | 1.389 Å |
| C (27) | C (28) | 1.393 Å | C (27) | C (35) | 1.526 Å |
| C (28) | C (29) | 1.359 Å | C (29) | C (30) | 1.400 Å |
| C (30) | C (31) | 1.456 Å | C (31) | C (32) | 1.495 Å |
| C (32) | C (33) | 1.576 Å | C (33) | C (34) | 1.494 Å |
| C (36) | C (37) | 1.420 Å | C (36) | C (41) | 1.409 Å |
| C (37) | C (38) | 1.365 Å | C (38) | C (39) | 1.396 Å |
| C (38) | C (46) | 1.550 Å | C (39) | C (40) | 1.423 Å |
| C (40) | C (41) | 1.400 Å | C (41) | C (42) | 1.460 Å |
| C (42) | C (43) | 1.512 Å | C (43) | C (44) | 1.556 Å |
| C (44) | C (45) | 1.501 Å | C (91) | C (92) | 1.525 Å |
| C (93) | C (94) | 1.510 Å | C (95) | C (96) | 1.491 Å |

No analogous process for the preparation of the novel crystalline complex compounds of formula I is described in in the literature.

Accordingly the invention also relates to a novel process for the preparation of the crystalline compounds of formula I, which comprises reacting a keto-acid of formula II

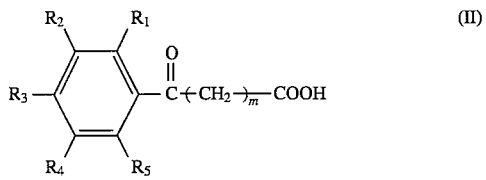

wherein the general symbols are as defined in formula I, with a morpholine derivative of formula III

wherein $R_{10}$ is as defined in formula I, without a solvent or in the presence of an aprotic solvent.

Not suitable for this process are protic solvents such as alcohols, typically methanol or ethanol.

Preferred reaction conditions for the novel process are the following:

It is preferred to heat a mixture of the keto-acid of formula II with a morpholine derivative of formula III to a homogeneous and clear melt. After cooling the melt to room temperature, the complex compounds of formula I crystallise out. The crystals are thereafter isolated by filtration and washed with a suitable solvent. The residue is then dried, giving the crystalline complex compounds of formula I in analytically pure form.

As may be inferred from Examples 1, 2 and 3, it is surprisingly of no consequence in this process in what molar ratio the keto-acid of formula II is used to the morpholine derivative of formula III. In each case the same crystalline 2:1 complex of formula I is isolated.

A preferred process, however, is that wherein the molar ratio of keto-acid of formula II to the morpholine derivative of formula III is 4:1 to 1:4, preferably 2:1 to 1:2, e.g. 1:1.

The reaction of both components is preferably carried out in an inert gas atmosphere, conveniently in nitrogen or argon.

The reaction or melt temperature in the novel process will depend on the physical properties of the keto-acid of formula II employed and on the morpholine derivative of formula III. A melt temperature of 40° to 130° C. is preferred, a more particularly preferred temperature range being from 50° to 120° C. A very particularly preferred melt temperature range for the preparation of the especially preferred crystalline complex compounds of formula I is from 60° to 80° C.

As soon as the reaction mixture has reached melt temperature and the melt is homogeneous and clear, stirring is preferably continued, prior to cooling, for only 1 to 20 minutes, preferably for 1 to 10 minutes, at this temperature.

The precipitated crystalline complex compounds of formula I are preferably washed during filtration with a readily volatile aprotic solvent of the hydrocarbon series, typically ligroin, pentane, hexane, hexane fractions or petroleum tractions. Hexane is particularly preferred.

The novel compounds of formula I are stable at room temperature and can be dried under atmospheric pressure or under a high vacuum. It is particularly preferred to dry the crystalline complex compounds of formula I in a drying oven in a water jet vacvuum in the temperature range from 20° to 30° C.

If the novel crystalline complex compounds are dried under more severe conditions, for example elevated temperature, the morpholine derivative of formula III partially volatilises and the novel 2:1 complex is partially destroyed. The dried product will still contain the novel crystalline complex compound of formula I, but is strongly contaminated with the free keto-acid of formula II.

The reaction of the keto-acid of formula II with a morpholine derivative of formula III can also be carried out in the presence of an aprotic solvent.

Suitable aprotic solvents are the same as those used for washing the products. Preferred solvents are hydrocarbons, typically benzene, toluene, xylene, ligroin, pentane, hexane, hexane fractions or white spirit. Particularly preferred aprotic solvents are aliphatic hydrocarbons, e.g. hexane. An excess of the compound of formula III can also be used as aprotic solvent.

A preferred reaction temperature in the inventive process using a solvent, for example a solvent of the hydrocarbon series, is the boiling temperature of the solvent.

The invention therefore also relates to products obtainable by reacting a keto-acid of formula II with a morpholine derivative of formula III without a solvent or in the presence of an aprotic solvent.

The keto-acids of formula II are known and some are commercially available or can be prepared in accordance with Houben-Weyl, Methoden der Organischen Chemie, Vol. VIII, pp. 381–382 (1952) and Vol. E5, pp. 398–399 (1985). Thus, for example, the Friedel-Crafts acylation of substituted aromatic hydrocarbons (benzene and naphthalene derivatives) with cyclic anhydrides affords the compounds of formula II in excellent yield.

The morpholine derivatives of formula III are known and some are commercially available or can be prepared as described in Houben-Weyl, Methoden der Organischen Chemie, Vol. XI/1, page 815 (1957).

The crystalline complex compounds of formula I are suitable corrosion inhibitors in coating compositions for protecting metallic surfaces. As such they can be added to all liquid or solid organic materials.

The invention thus also relates to coating compositions comprising a) an organic film forming binder and b) as corrosion inhibitor, a crystalline complex compound of formula I.

The coating composition is preferably a paint system. An aqueous paint system is particularly preferred.

Paint systems are typically lacquers, paints or varnishes. These systems always contain an organic film-forming binder together with other optional components.

Suitable film-forming binders for the coating compositions are all conventional film-formers for solvent-based or solventless, but preferably aqueous, paint systems. Illustrative examples of such film-formers are epoxy resins, polyurethane resins, aminoplast resins or mixtures of resins; a basic aqueous dispersion or a solution of an acid resin.

Preferred organic film-forming binders are epoxy resins, polyurethane resins, polyester resins, acrylic resins and their copolymer resins, polyvinyl resins, phenolic resins, alkyd resins, or mixtures of such resins.

Particularly interesting organic film-forming binders for aqueous coating compositions are e.g. alkyd resins, bicomponent epoxy resins, polyurethane resins, polyester resins which are usually saturated, water-dilutable phenolic resins or derived dispersions; water-dilutable urea resins; resins based on vinyl/acrylic copolymers.

More specifically, the alkyd resins may be water-dilutable alkyd resin systems which can be used as air-drying systems or in the form of storing systems, optionally in conjunction with water-dilutable melamine resins. They may also be oxidatively drying, air-drying or stoving systems which are optionally used in conjunction with aqueous dispersions based on acrylic resins or their copolymers, with vinyl acetates and the like.

The acrylic resins may be pure acrylic resins, acrylate copolymers, combinations with vinyl resins or copolymers with vinyl monomers such as vinyl acetate, styrene or butadiene. These systems can be air-drying systems or stoving systems.

Water-dilutable epoxy resins in conjunction with suitable polyamine crosslinking agents exhibit excellent mechanical and chemical resistance. When using liquid epoxy resins, the addition of organic solvents to aqueous systems can be dispensed with. The use of solid resins or solid resin dispersions usually requires an addition of minor amounts of solvent to enhance the film formation.

Preferred epoxy resins are those derived from aromatic polyols, especially from bisphenols. The epoxy resins are used in conjunction with crosslinking agents. These latter may preferably be amino- or hydroxy-functional compounds, an acid, an acid anhydride or a Lewis acid. Typical examples are polyamines, polyaminoamides, polymers based on polysulfides, polyphenols, boron fluorides and their complex compounds, polycarboxylic acids, 1,2-dicarboxylic anhydrides or pyromellitic dianhydride.

Polyurethane resins are derived from polyethers, polyesters and polybutadienes carrying hydroxyl end groups on the one hand, and aliphatic or aromatic polyisocyanates on the other.

Suitable polyvinyl resins are typically polyvinyl butyral, polyvinyl acetate or their copolymers.

Suitable phenolic resins am synthetic resins of which phenols form the main component, i.e. in particular phenol-, cresol-, xylenol- and resorcinol-formaldehyde resins, alkyl phenol resins as well as condensates of phenols with acetaldehyde, furfurol, acrolein or other aldehydes. Modified phenolic resins are also of interest.

The coating compositions may additionally comprise one or more than one component selected from the group consisting of pigments, dyes, fillers, flow control agents, dispersants, thixotropic agents, adhesion promoters, antioxidants, light stabilisers or curing catalysts. They may also comprise still other known corrosion inhibitors, for example anticorrosion pigments such as phosphate or borate-containing pigments or metal oxide pigments, or other organic or inorganic corrosion inhibitors, e.g. salts of nitroisophthalic acid, phosphorus esters, technical amines or substituted benzotriazoles.

Illustrative examples of additional pigments are titanium dioxide, iron oxide, aluminium bronze or phthalocyanine blue.

Illustrative examples of additional fillers are talcum, alumina, aluminium silicate, barytes, mica or silica.

Flow control agents and thixotropic agents may be those based on modified bentonites.

Adhesion promoters are based on modified silanes.

It is also advantageous to add basic fillers or pigments which, in specific binder systems, have a synergistic effect on corrosion inhibition. Illustrative examples of such basic fillers and pigments are calcium or magnesium carbonate, zink oxide, zinc carbonate, zinc phosphate, magnesium oxide, alumina, aluminium phosphate or mixtures thereof. Examples of basic organic pigments are those based on aminoanthraquinone.

The novel corrosion inhibitors can be added to the paint system during the preparation thereof, conveniently during the pigment distribution by milling or during the extrudation process in the case of powder coating compositions, or the inhibitor is dissolved in a solvent and the solution is then stirred into the coating composition.

The novel crystalline complex compounds of formula I are conveniently used in an amount of 0.02 to 20% by weight, preferably 0.1 to 10% by weight, based on the weight of the total solids content of the coating composition.

The paint formulations can be applied to the substrate by conventional methods, conveniently by spraying, dipping, brushing, electrostatic spraying or electrodeposition. Often a plurality of layers is applied. The corrosion inhibitors are preferably added to the primer, as they act in particular at the metal/coating interface. They can, however, also be added to the interlayer or topcoat. Depending on whether the binder is a physically, chemically or oxidatively drying resin or a thermosetting or radiation-curing resin, the cure of the coating is carried out at room temperature or by heating (stoving) or irradiation.

The paint system is preferably a primer for metallic substrates such as iron, steel, copper, zinc or aluminium, as well as alloys thereof.

In addition to the anticorrosive action, the crystalline complex compounds of formula I have the advantage that they promote the adhesion of the coating to a metal substrate and have no adverse effect on the shelf-stability of the novel coating compositions.

A preferred embodiment of the invention is therefore the use of the crystalline complex compounds of formula I as corrosion inhibitors in coating compositions for metallic surfaces.

The invention further relates to a method of protecting a corrodible metallic substrate, which comprises applying to said substrate a coating composition which comprises a) an organic film-forming binder, and b) as corrosion inhibitor, at least one crystalline complex compound of formula I, and subsequently drying and/or curing the coated substrate.

The invention is illustrated by the following Examples in which parts and percentages are by weight.

EXAMPLE 1

Preparation of the crystalline complex of 3-(4-methylbenzoyl)propionic acid with excess N-ethylmorpholine [compound (101)]

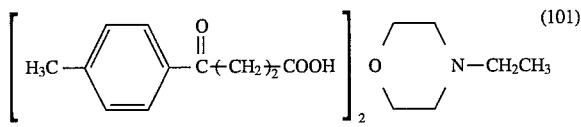

11.5 g (0.10 mol) of N-ethylmorpholine and 9.60 g (0.05 mol) of 3-(4-methylbenzoyl)propionic acid are heated at 60° C. in a nitrogen atmosphere. The homogeneous, clear reaction solution is stirred for 10 minutes to 60° C. and then cooled, with stirring, to room temperature. The precipitate is isolated by filtration, washed well repeatedly with hexane and dried at 30° C. in a vacuum drying oven, affording 11.8 g of white crystals of compound (101), m.p. 66°–68° C. Elemental analysis is in accord with the composition $C_{11}H_{12}O_3 \cdot 0.5\ C_6H_{13}NO$. Calculated: C 67.31; H 7.47; N 2.80%; found: C 67.57; H 7.39; N 2.55%.

This compound (101) was subjected to X-ray structural analysis. The crystalline complex compound (101) melts at 66°–68° C. The crystals are large and often intergrown. They are obtained in the form of "milk glass" coloured flakes. The thinner specimens are clearer. To measure a large crystal, an optically perfect fragment is separated with a razor blade and bonded with ®Araldit Rapid (Ciba-Geigy) to a MARK glass capillary. The crystal fragment is coated with the same adhesive. Orientation micrographs (Polaroid) taken on a Precession goniometer show—for a crystal with such a low melting point—a good reflectance quality and a normal diffusion coefficient. The unit cells, the crystal system and the space group are determined in a diffractometer. The crystal remains very stable to the end during the 9-day duration of the experiment.

Size of the monocrystal fragment (mm): 0.90 × 0.72 × 0.20
crystal system: monoclinic
space group: $P2_1/n$ (centrosymmetric)

| a = 28.466 Å | b = 9.623 Å | c = 31.246 Å |
|---|---|---|
| | β = 111.73° | |
| | Z = 4 | |
| volume = 7950.9 Å³ | density = 1.252 g/cm³ (calcd.) | |

The measurements were carried out on a Philips PW1100 diffractometer with $MoK\alpha_1$ radiation (=0.70926 Å).

reflection width: 1.4° measuring times: background 2×10", reflexes 36–42"

measuring conditions: Θ-2Θ-scanning method $MoK\alpha_1$ radiation, 50 kV, 35 mA, graphite monochromator, scaling: by measuring 3 reference reflexes after every 2 hours measuring range: 10750 reflexes were measured from 2Θ6°–44°. Of these, 3482 were taken as observed $(I>2\sigma(I))$.

EXAMPLE 2

Preparation of the crystalline complex of 3-(4-methylbenzoyl)propionic acid with a less than equivalent amount of N-ethylmorpholine [compound (101)].

2.88 g (0.025 mol) of N-ethylmorpholine and 9.60 g (0.05 mol) of 3-(4-methylbenzoyl)propionic acid are heated to 70°–75° C. in a nitrogen atmosphere. As soon as a clear melt is obtained, the melt is cooled to room temperature. The solid reaction mass is stirred with hexane, the precipitated crystals are isolated by filtration, washed with hexane, and dried in a vacuum drying oven at 30° C., affording 12.2 g of light brown crystals of compound (101), m.p. 65°–67° C. Elemental analysis is in accord with the composition $C_{11}H_{12}O_3 \cdot 0.5\ C_6H_{13}NO$. Analysis: calculated: C 67.31; H 7.47; N 2.80%; found: C 67.35; H 7.38; N 2.47%.

EXAMPLE 3

Preparation of the crystalline complex of 3-(4-methylbenzoyl)propionic acid with excess N-ethylmorpholine in the presence of hexane as solvent [compound (101)].

5.76 g (0.05 mol) of N-ethylmorpholine and 4.8 g (0.025 mol) of 3-(4-methylbenzoyl)propionic acid are added to 20 ml of hexane in a nitrogen atmosphere and the mixture is heated to reflux temperature. After c. 30 minutes the mixture is cooled to room temperature, with stirring. The precipitate is isolated by filtration, washed with hexane and dried at 30° C. in a vacuum drying oven at 30° C., affording 5.9 g of white crystals of compound (101), m.p. 66°–68° C. Elemental analysis is in accord with the composition $C_{11}H_{12}O_3 \cdot 0.5\ C_6H_{13}NO$. Analysis: calculated: C 67.31; H 7.47; N 2.80%; found: C 67.45; H 7.42; N 2.58%.

EXAMPLE 4

Preparation of the crystalline complex of 3-(4-methylbenzoyl)propionic acid with N-methylmorpholine [compound (102)].

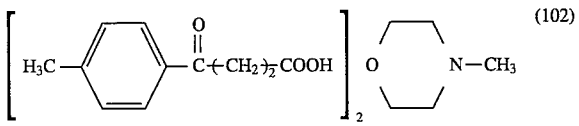

5.05 g (0.05 mol) of N-methylmorpholine and 9.60 g (0.05 mol) of 3-(4-methylbenzoyl)propionic acid are heated to 70° C. in a nitrogen atmosphere. As soon as a clear melt is obtained, the melt is cooled to room temperature. The reaction mass is stirred with hexane, the precipitated crystals are isolated by filtration, washed with hexane, and dried at 20° C. in a vacuum drying oven, affording 8.5 g of beige crystals of compound (102), m.p. 67°– 68° C. Elemental analysis is in accord with the composition $C_{11}H_{12}O_3 \cdot 0.5 C_5H_{11}NO$. Analysis: calculated: C 66.79; H 7.27; N 2.88%; found: C 66.54; H 7.30; N 2.88%.

EXAMPLE 5

Preparation of the crystalline complex of 3-(4-methylbenzoyl)propionic acid with N-isobutylmorpholine [compound (103)].

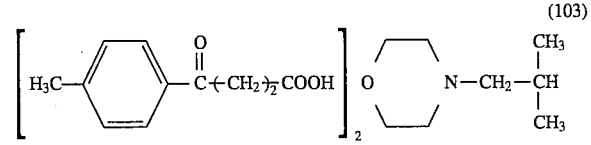

7.16 g (0.05 mol) of N-isobutylmorpholine and 9.60 g (0.05 mol) of 3-(4-methylbenzoyl)propionic acid are heated to 60° C. in a nitrogen atmosphere. The homogeneous, clear reaction solution is stirred for 10 minutes at 60° C. and then cooled to room temperature, with stirring. The precipitate is isolated by filtration, washed well repeatedly with hexane, and dried in a vacuum drying oven at 20° C., affording 12.8 g of pinkish-yellow crystals of compound (103), m.p. 69°–71° C. Elemental analysis is in accord with the composition $C_{11}H_{12}O_3.0.5\ C_8H_{17}NO$. Analysis: calculated: C 68.29; H 7.83; N 2.65%; found: C 68.28; H 7.81; N 2.55%.

EXAMPLE 6

Preparation of the crystalline complex of 3-(4-methylbenzoyl)propionic acid with N-n-butylmorpholine [compound (104)].

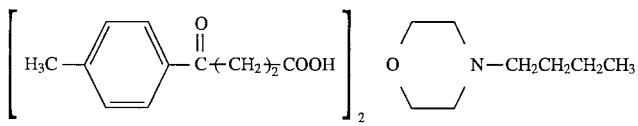

(104)

7.16 g (0.05 mol) of N-n-butylmorpholine and 4.80 g (0.025 mol) of 3-(4-methylbenzoyl)propionic acid are heated to 60° C. in a nitrogen atmosphere. The homogeneous, clear reaction solution is stirred for 30 minutes at 60° C. and then cooled to room temperature, with stirring. The precipitate is isolated by filtration, washed well repeatedly with hexane, and dried in a vacuum drying oven at 20° C., affording 5.6 g of beige crystals of compound (104), m.p. 58°–60° C. Elemental analysis is in accord with the composition $C_{11}H_{12}O_3.0.5\ C_8H_{17}NO$. Analysis: calculated: C 68.29; H 7.83; N 2.65%. found: C 67.58; H 7.82; N2.78%.

EXAMPLE 7

Preparation of the crystalline complex of 3-(4-chlorobenzoyl)propionic acid with N-ethylmorpholine [compound (105)].

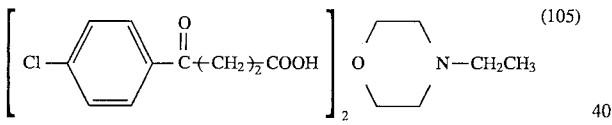

(105)

2.90 g (0.025 mol) of N-ethylmorpholine and 5.30 g (0.025 mol) of 3-(4-methylbenzoyl)propionic acid are heated to 70° C. in a nitrogen atmosphere. The homogeneous, clear reaction solution is stirred for 10 minutes at 60° C. and then cooled to room temperature, with stirring. The precipitate is isolated by filtration, washed well repeatedly with hexane, and dried in a vacuum drying oven at 20° C., affording 6.0 g of white crystals of compound (105), m.p. 77°–79° C. Elemental analysis is in accord with the composition $C_{10}H_9O_3Cl.\ 0.5\ C_6H_{13}NO$. Analysis: calculated: C 57.78; H 5.78; N 2.59; Cl 13.12%. found: C 57.88; H 5.75; N 2.51; Cl 3.22%.

EXAMPLE 8

Preparation of the crystalline complex of 3-(4-phenylbenzoyl)propionic acid with N-ethylmorpholine [compound (106)].

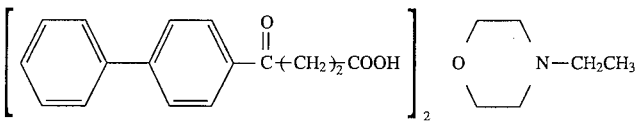

(106)

2.90 g (0.025 mol) N-ethylmorpholine and 3.20 g (0.025 mol) of 3-(4-phenylbenzoyl)propionic acid are heated to 120° C. in a nitrogen atmosphere. The homogeneous, clear reaction solution is stirred for 10 minutes at 120° C. and then cooled to room temperature, with stirring. The solid reaction mass is stirred in hexane, the precipitated crystals are isolated by filtration, washed with hexane and dried in a vacuum drying oven at 20° C., affording 3.8 g of white crystals of compound (106), m.p. 105°–107° C. Elemental analysis is in accord with the composition $C_{16}H_{14}O_3.0.5\ C_6H_{13}NO$. Analysis: calculated: C 73.17%; H 6.63%; N 2.25%. found: C 73.00%; H 6.68%; N 2.24%.

EXAMPLE 9

Assay of the crystalline complex of 3-(4-methylbenzoyl) propionic acid with N-ethylmorpholine [compound (101)] in water-dilutable 2K-epoxy resin anticorrosion primer based on Beckopox EP 384 W/Beckopox EP 075/Beckopox EH 623 W as corrosion inhibitor.

To prepare the coating composition based on Beckopox EP 384 W/Beckopox EP 075/Beckopox EH 623 W, components 1 to 8 (formulation without additives) and components 1 to 9 (formulation with additive) are used in the order shown (component A, cf. Table 2).

TABLE 2

Water-dilutable 2K-epoxy resin anticorrosion primer based on
Beckopox EP 384 W/Beckopox EP 075/Beckopox EH 623 W

| Formulation | Example 9a % by weight | Example 9b % by weight |
|---|---|---|
| Component A: | | |
| 1) Beckopox EH 623 W(80% physical form)[a] | 14.4 | 14.4 |
| 2) deion. water | 29.2 | 29.2 |
| 3) talcum AT Extra[b] | 13.8 | 13.8 |
| 4) Bayferrox 130M[c] | 12.0 | 12.0 |
| 5) Millicarb[d] | 27.3 | 27.3 |
| 6) Bentone SD 2[e] | 0.70 | 0.70 |
| 7) Borchigel L 75 (25% physical form)[f] | 1.70 | 1.70 |
| 8) Additol XL 270[g] | 0.9 | 0.9 |
| 9) corrosion inhibitor (compound (101)) | — | 3.10 |
| Total | 100.00 | 103.10 |
| Component B: | | |
| 10) Beckopox EP 384 W(54% physical form)[h] | 63.0 | 63.0 |
| 11) Beckopox EP 075[i] | 3.7 | 3.7 |

[a] ®Beckopox EH 623 W: polyamine hardener (Hoechst AG);
[b] ®Talkum AT Extra: Norwegian;
[c] ®Bayferrox 130M: iron oxide red (Bayer AG);
[d] ®Millicarb: calcium carbonate (Omya);
[e] ®Bentone SD 2: antiprecipitant (Kronos Titan GmbH);
[f] ®Borchigel L 75: thickener/rheology enhancer (Gebr. Botchers AG);
[g] ®Additol XL 270: antiflooding agent/dispersant(Hoechst AG);
[h] ®Beckopox EP 384 W: epoxy resin (Hoechst AG);
[i] ®Beckopox EP 075: reactive diluent (polypropylene glycol diglycidyl ether The resultant component A (formulation with and without corrosion inhibitor) is dispersed in a horizontal ball mill to a particle size of <15 μm. The dispersing result is evaluated by determining the grindometer value (ISO 1524).

For application, 100 g (formulation without corrosion inhibitor, Example 9a) and 103.1 g (formulation with corrosion inhibitor, Example 9b) are mixed with 66.7 g of component B. To adjust to the desired spraying consistency, the paint formulation is diluted with demineralised water. The paint samples are applied to rolled steel plates (19×10.5 cm) of the Bonder type (cold rolled, degreased steel; manufacturer: Chemetall, Frankfurt am Main/Germany) in a layer thickness of 60 μm after drying (drying conditions: 10 days at room temperature).

Before the start of weathering, a parallel cut (i.e. parallel to the longest edge of the steel plate) is made on the "paint films" using a Bonder cross-cut apparatus (Mod. 205; supplier: Lau, Hemer/Germany) as a defined damage of the coating. The edges of the steel plates am protected by applying an edge protector (®Icosit 255; supplier: Inertol AG, Winterthur, Switzerland).

The samples are then subjected to a rapid weathering by a salt-spray test procedure (DIN 50 021 SS) for 190 hours and to a humidity test (ASTM D 4585-87) for 168 hours. The results are set forth in Tables 3 and 4. The evaluation of the results is made on the basis of the relevant DIN standards in accordance with a rating scheme by indicating a CPF ("Corrosion Protection Factor). The CPF is given by the sum of the assessment of the coating and the steel and is at most 12 points. The individual maximum values for the coating and the steel are 6 points. The higher these values are, the better the corrosion inhibition.

TABLE 3

| | Salt spray test, 190 hours | | |
|---|---|---|---|
| Coating composition | CPF Coating | CPF Metal | CPF |
| Example 9a | 2.4 | 1.3 | 3.7 |
| Example 9b | 4.2 | 5.2 | 9.4 |

TABLE 4

| | Humidity test, 168 hours | | |
|---|---|---|---|
| Coating composition | CPF Coating | CPF Metal | CPF |
| Example 9a | 2.8 | 2.0 | 4.8 |
| Example 9b | 4.8 | 6.0 | 10.8 |

EXAMPLE 10

Assay of the crystalline complex of 3-(4-methylbenzoyl) propionic acid with N-ethylmorpholine [compound (101)] in aqueous dispersion based on an acrylate/styrene copolymer(Acronal S 760) as corrosion inhibitor.

To prepare the coating composition based on Acronal S 760, components 1 to 5 are first premixed, then components 6 and 7 are added (formulation without corrosion inhibitor) and 6 to 8 (formulation with corrosion inhibitor, compound (101), Example 1) in the order shown (q.v. Table 5).

TABLE 5

Aqueous dispersion based on Acronal S 760

| Formulation | Example 10a % by weight | Example 10b % by weight |
|---|---|---|
| 1) deion. water | 8.20 | 8.20 |
| 2) pigment dispersant NL[a)] | 0.15 | 0.15 |
| 3) Acronal S 760 (50% physical form)[b)] | 8.00 | 8.00 |
| 4) Shellsol D 60[c)] | 1.00 | 1.00 |
| 5) Agitan 280[d)] | 0.30 | 0.30 |
| 6) Millicarb[e)] | 18.00 | 18.00 |
| 7) Bayferrox 130M[f)] | 10.00 | 10.00 |
| 8) corrosion inhibitor (compound (101)) | — | 1.14 |
| 9) Acronal S-760 (50% physical form)[b)] | 49.00 | 49.00 |
| 10) Agitan 280[d)] | 0.30 | 0.30 |
| 11) Collacral PU 85/butyl diglycol[g)] | 4.10 | 4.10 |
| 12) deion. water | 0.95 | 0.95 |
| Total | 100.00 | 101.14 |

[a)]® Pigment dispersant NL: BASF AG;
[b)]® Acronal S 760: acrylate-styrene copolymer (aqueous dispersion, BASF AG);
[c)]® Shellsol D 60: white spirit (Shell);
[d)]® Agitan 280: defoamer (Münzing Chemie GmbH);
[e)]® Millicarb: calcium carbonate (Firma Omya);
[f)]Bayferrox 130M: iron oxide red (Bayer AG);
[g)]® Collacral PU 85: thickener (BASF AG).

The resultant pigment paste is dispersed in a horizontal ball mill or the like to a particle size of <15 μm. The particle size is evaluated from the grindometer value (ISO 1524).

To finish the paint formulation (reduction), components 9 to 12 are added in the order shown (Table 5). The paint formulation is applied by conventional spraying. Depending on the desired viscosity, the finished paint formulation can be diluted by butyl diglycol/deionised water (1:1 g/g).

The paint formulation is applied as described in Example 9 to steel plates of the Bonder type in a layer thickness which, after drying, is 100 μm (drying conditions: 14 days at room temperature).

Before the start of weathering, a parallel cut (i.e. parallel to the longest edge of the steel plate) is made on the "paint films" using a Bonder cross-cut apparatus (Mod. 205; supplier: Lau, Hemer/Germany) as a defined damage of the coating. The edges of the steel plates are protected by applying an edge protector (®Icosit 255; supplier: Inertol AG, Winterthur, Switzerland).

The samples are then subjected to a rapid weathering by a salt-spray test procedure (DIN 50 021 SS) for 168 hours. The results are summarised in Table 6. The evaluation of the results is made on the basis of the relevant DIN standards in accordance with a rating scheme by indicating a CPF ("Corrosion Protection Factor). The CPF is given by the sum of the assessment of the coating and the steel and is at most 12 points. The individual maximum values for the coating and the steel are 6 points. The higher these values are, the better the corrosion inhibition.

TABLE 6

Salt spray test (DIN 50 021 SS), 168 hours

| Coating composition | CPF Coating | CPF Metal | CPF |
|---|---|---|---|
| Example 10a | 2.4 | 2.6 | 5.0 |
| Example 10b | 4.1 | 5.8 | 9.9 |

EXAMPLE 11

Assay of the crystalline complex of 3-(4-methylbenzoyl-)propionic acid with N-ethylmorpholine [compound (101)] in aqueous acrylic dispersion (Maincote HG-54) as corrosion inhibitor.

To prepare the coating composition on the basis of Maincote HG-54, components 1 to 8 (formulation without corrosion inhibitor) and 1 to 9 (formulation with corrosion inhibitor) are used in the order shown (q.v. Table 7).

TABLE 7

Acrylic dispersion based on Maincote HG-54

| Formulation | % by weight |
|---|---|
| 1) deion. water | 3.10 |
| 2) methyl carbitol[a)] | 5.00 |
| 3) Orotan 165[b)] | 0.82 |
| 4) Triton CF 10[c)] | 0.29 |
| 5) Drew Plus TS 4380[d)] | 0.28 |
| 6) Acrysol RM 8[e)] | 0.60 |
| 7) Bayferrox 130M[f)] | 5.72 |
| 8) Millicarb[g)] | 17.40 |
| 9) inventive corrosion inhibitor | |
| 10) butyl diglycol | 3.67 |
| 11) Maincote HG-54[h)] | 58.70 |
| 12) Texanol[i)] | 1.50 |
| 13) dibutyl phthalate[k)] | 1.50 |
| 14) sodium nitrite (13.8% in $H_2O$)[l)] | 0.80 |
| 15) Drew T 4310[m)] | 0.32 |
| 16) ammonia solution (25%) | 0.30 |
| Total | 100.00 |

Total solids content: 47%; pH: 8 to 8.5;
[a)]® methyl carbitol: diethylene glycol monomethyl ether (Union Carbide);
[b)]® Orotan 165: dispersant (Rohm & Haas);
[c)]Triton CF 10: nonionic wetting agent (Rohm & Haas);
[d)]® Drew Plus TS 4380: defoamer (Drew Chem. Corp.);
[e)]® Acrysol RM 8: nonionic thickener (Rohm & Haas);
[f)]® Bayferrox 130M: iron oxide red (Bayer AG);
[g)]® Millicarb: calcium carbonat (Omya);
[h)]® Maincote HG-54: acrylic dispersion, 41.5% in deionised water (Rohm & Haas);
[i)]® Texanol: coalescent (Eastman Chem. Prod., Inc.);
[k)]dibutyl phthalate: plasticiser (Eastman Chem. Prod., Inc.);
[l)]sodium nitrite: rust inhibitor (Fluka);
[m)]® Drew T 4310: nonionic defoamer (Drew Chem. Corp.).

Components 1 to 8 and 1 to 9 are dispersed with an impeller at 3000 rpm to a particle size of <15 μm. The particle size of the pigment paste is determined from the grindometer value (ISO 1524). The amount of novel corrosion inhibitor is based on the total solids content of the formulation without additive (total solids content: 47% ). Accordingly, the addition of 1% of corrosion inhibitor in 100 g of dispersion corresponds to an amount of 0.47 g. The coating composition is finished by adding components 10 to 16 as shown in Table 7 at a reduced stirring rate (1000 rpm) in the order shown. The pH of the formulation is checked and, before application, adjusted if necessary with ammonia solution (25%) to pH 8–8.5.

The coating composition can be applied by airless spraying, brushing, roller coating or, after dilution, by conventional spraying. Dilution to the desired spraying consistency is effected by addition of butyl glycol/water (1:1 g/g). In the subsequent Example, the coating composition is applied in accordance with Examples 9 to 11 by conventional spraying.

The formulation is applied to rolled steel plates (19×10.5 cm) of the Bonder type (cold rolled, degreased steel; manufacturer: Chemetall, Frankfurt am Main/Germany) in a layer thickness of 50–55 μm after drying (drying conditions: 10 days at room temperature).

Before the start of weathering, a parallel cut (i.e. parallel to the longest edge of the steel plate) is made on the "paint films" using a Bonder cross-cut apparatus (Mod. 205; supplier: Lau, Hemer/Germany) as a defined damage of the coating. The edges of the steel plates are protected by applying an edge protector (®Icosit 255; supplier: Inertol AG, Winterthur, Switzerland).

The samples are then subjected to a rapid weathering by a salt-spray test procedure (DIN 50 021 SS) for 168 hours and to a humidity test (ASTM D 4585-87) over 330 hours. The results are set forth in Tables 8 and 9. The evaluation of the results is made on the basis of the relevant DIN standards in accordance with a rating scheme by indicating a CPF ("Corrosion Protection Factor). The CPF is given by the sum of the assessment of the coating and the steel and is at most 12 points. The individual maximum values for the coating and the steel are 6 points. The higher these values are, the better the corrosion inhibition.

TABLE 8

| | Salt spray test, 168 hours | | |
|---|---|---|---|
| Compound | CPF Coating | CPF Metal | CPF |
| — | 2.8 | 2.0 | 4.8 |
| 2% (101) | 4.6 | 4.7 | 9.3 |
| 3% (101) | 4.6 | 4.7 | 9.3 |

TABLE 9

| | Humidity test, 330 hours | | |
|---|---|---|---|
| Compound | CPF Coating | CPF Metal | CPF |
| — | 3.0 | 0.6 | 3.6 |
| 2% (101) | 2.2 | 5.8 | 8.0 |
| 3% (101) | 3.0 | 5.8 | 8.8 |

EXAMPLE 12

Assay of the crystalline complex of 3-(4-methylbenzoyl)propionic acid with N-ethylmorpholine [compound (111)] in water-dilutable alkyd/urethane primers based on Resydrol AZ 436 W/Daotan VTW 1237 as corrosion inhibitor.

To prepare the coating composition based on Resydrol AZ 436 W/Daotan VTW 1237, components 1 to 12 are used in the order shown (q.v. Table 10).

TABLE 10

Water-dilutable alkyd/urethane primer based on Resydrol AZ 436 W/Daotan VTW 1237

| Formulation | % by weight |
|---|---|
| Part 1: | |
| 1) Resydrol AZ 436 W (45% physical form)[a] | 28.3 |
| 2) ammonia solution (10%) | |
| 3) Additol VXW 4940 (1:1 in water)[b] | 0.6 |
| Resydrol AZ 436 W is neutralised with the ammonia solution to pH = 8.5, then Additol VXW 4930 is dispersed in the mixture | |
| Part 2: | |
| 4) Daotan VTW 1237 (32% physical form)[c] | 39.8 |
| Part 2 is stirred into part 1, then the pH is checked and, if necessary, adjusted with ammonia solution to pH 8.5. | |
| Part 3: | |
| 5) Surfynol SE[d] | 0.3 |
| 6) Additol VXW 4973[e] | 0.3 |
| 7) Borchigel L 75 (25% physical form)[f] | 2.0 |
| 8) Mikrotalk AT Extra[g] | 7.3 |
| 9) Bayferrox 130M[h] | 6.4 |
| 10) Millicarb[i] | 11.8 |
| 11) inventive corrosion inhibitor | |
| 12) deion. water | 3.2 |
| Total | 100.0 |

[a]® Resydrol AZ 436 W: alkyd resin emulsion (Hoechst AG);
[b]® Additol VXW 4940: solid (metal drying agent based on Co, Zr, Ba)(Hoechst AG);
[c]® Daotan VTW 1237: polyurethane emulsion (Hoechst AG);
[d]® Surfynol SE: nonionic wetting agent (Air Products and Chemicals);
[e]® Additol VXW 4973: defoamer (Hoechst AG);
[f]® Borchigel L thickener 75: (Gebrüder Borchers AG);
[g]® Microtalk AT Extra: micronised talcum (Norwegian);
[h]® Bayferrox 130M: iron oxide red (Bayer AG);
[i]® Millicarb: calcium carbonate (Firma Omya).

To prepare the coating composition based on Resydrol AZ 436 W/Daotan VTW 1237, Resydrol AZ 436 W (component 1) is first adjusted with ammonia solution (component 2) to pH=8.5. Then component 3 is thoroughly dispersed in the mixture. Daotan VTW 1237 (component 4) is stirred in after the addition of components 1 to 3, the pH is checked and, if necessary, adjusted with ammonia solution to pH=8.5. Components 5 to 12 are then added in the order shown, and the batch is only predispersed. After standing overnight, the composition is dispersed to a particle size of <15 μm. The particle size is determined from the grindometer value (ISO 1524). The amount of inventive corrosion inhibitor is based on the total solids content of the formulation without corrosion inhibitor (total solids content: 51%). Accordingly, addition of 1% of corrosion inhibitor to 100 g of primer denotes an amount of 0.51 g.

For conventional spraying, the paint formulation is adjusted with deionised water to the desired spraying consistency.

The paint formulation is applied to rolled steel plates (19×10.5 cm) of the Bonder type (cold rolled, degreased steel; manufacturer: Chemetall, Frankfurt am Main/Germany) in a layer thickness of 50–55 μm after drying (drying conditions: 14 days at room temperature).

Before the start of weathering, a parallel cut (i.e. parallel to the longest edge of the steel plate) is made on the "paint films" using a Bonder cross-cut apparatus (Mod. 205; supplier: Lau, Hemer/Germany) as a defined damage of the coating. The edges of the steel plates are protected by applying an edge protector (®Icosit 255; supplier: Inertol AG, Winterthur, Switzerland).

The samples are then subjected to a rapid weathering by a salt-spray test procedure (DIN 50 021 SS) for 120 hours. The evaluation of the corrosion inhibition CPF is made according to Example 11. The results are set forth in Table 11. The higher the values are, the better the corrosion inhibition.

TABLE 11

| | Salt spray test, 120 hours | | |
|---|---|---|---|
| Compound | CPF Coating | CPF Metal | CPF |
| — | 2.0 | 2.5 | 4.5 |
| 2% (101) | 3.8 | 4.5 | 8.3 |

What is claimed is:

1. A crystalline complex compound of formula I

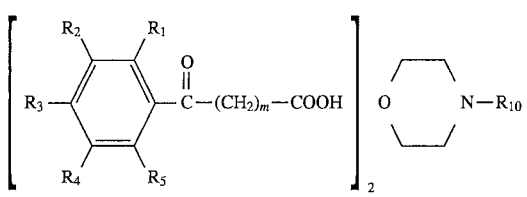
(I)

wherein $R_1$, $R_2$, $R_3$, $R_4$ and $R_5$ are each independently of one another hydrogen, halogen, nitro, cyano, $CF_3$, $C_1$–$C_{15}$alkyl, $C_5$–$C_{12}$cycloalkyl, $C_2$–$C_{15}$alkenyl, $C_1$–$C_{12}$haloalkyl, $C_1$–$C_{12}$alkoxy, $C_1$–$C_{12}$alkylthio, unsubstituted or $C_1$–$C_4$alkyl-substituted $C_6$–$C_{10}$aryl; unsubstituted or $C_1$–$C_4$alkyl-substituted $C_6$–$C_{10}$aryloxy; unsubstituted $C_7$–$C_{12}$arylalkyl or $C_7$–$C_{12}$arylalkyl which is substituted in the aryl moiety by 1 to 3 $C_1$–$C_4$alkyl groups;

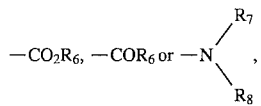

with the proviso that at least one of $R_1$ to $R_5$ is hydrogen, halogen or $C_1$–$C_{15}$alkyl; and each pair of substituents $R_1$ and $R_2$, $R_2$ and $R_3$, $R_3$ and $R_4$ or $R_4$ and $R_5$, together with the linking carbon atom, form a benzene or cyclohexenyl ring, $R_6$ is $C_1$–$C_{20}$alkyl, $C_2$–$C_{20}$alkyl which is interrupted by oxygen, sulfur or

unsubstituted $C_7$–$C_{12}$arylalkyl or $C_7$–$C_{12}$arylalkyl which is substituted in the aryl moiety by 1 to 3 $C_1$–$C_4$alkyl groups;

$R_7$ and $R_8$ are each independently of the other hydrogen, $C_1$–$C_{24}$alkyl or $C_2$–$C_{24}$alkyl which is interrupted by oxygen, sulfur or

$R_9$ is hydrogen or $C_1$–$C_8$alkyl, $R_{10}$ is $C_1$–$C_{15}$alkyl, $C_2$–$C_{20}$alkyl which is interrupted by oxygen, sulfur or

$C_5$–$C_{12}$cycloalkyl, $C_2$–$C_{15}$alkenyl, $C_1$–$C_{12}$alkoxy, $C_1$–$C_{12}$alkylthio, unsubstituted or $C_1$–$C_4$ alkyl-substituted $C_6$–$C_{10}$aryl; unsubstituted or $C_1$–$C_4$alkyl-substituted $C_6$–$C_{10}$aryloxy; unsubstituted $C_7$–$C_{12}$arylalkyl or $C_7$–$C_{12}$arylalkyl which is substituted in the aryl moiety by 1 to 3 $C_1$–$C_4$alkyl groups; and m is an integer from 2 to 5.

2. A crystalline complex compound according to claim 1, wherein at least two of $R_1$ to $R_5$ are hydrogen.

3. A crystalline complex compound according to claim 1, wherein $R_1$ is hydrogen, $R_2$, $R_3$, $R_4$ and $R_5$ are each independently of one another hydrogen, chloro, bromo, nitro, cyano, $CF_3$, $C_1$–$C_8$alkyl, $C_5$–$C_7$cycloalkyl, $C_3$–$C_8$alkenyl, $C_1$–$C_8$alkoxy, $C_1$–$C_8$alkylthio, phenyl, phenoxy, benzyl,

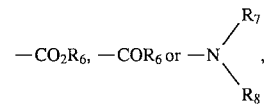

$R_6$ is $C_1$–$C_{12}$alkyl, $C_2$–$C_{12}$alkyl which is interrupted by oxygen; or benzyl, and $R_7$ and $R_8$ are each independently of the other hydrogen, $C_1$–$C_8$alkyl or $C_2$–$C_{12}$alkyl which is interrupted by oxygen.

4. A crystalline complex compound according to claim 1, wherein $R_{10}$ is $C_1$–$C_8$alkyl, $C_3$–$C_{12}$alkyl which is interrupted by oxygen or sulfur; $C_5$–$C_7$cycloalkyl, $C_3$–$C_8$alkenyl, $C_1$–$C_8$alkoxy, $C_1$–$C_8$alkylthio, phenyl, phenoxy or benzyl.

5. A crystalline complex compound according to claim 1, wherein $R_1$, $R_2$ and $R_4$ are hydrogen, $R_3$ and $R_5$ are each independently of the other hydrogen, chloro, bromo, $CF_3$, $C_1$–$C_8$alkyl, cyclohexyl, $C_1$–$C_8$alkoxy, phenyl,

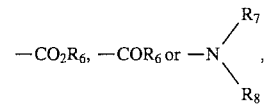

$R_6$ is $C_1$–$C_8$alkyl, $R_7$ and $R_8$ are each independently of the other hydrogen or $C_1$–$C_8$alkyl, $R_{10}$ is $C_1$–$C_8$alkyl, cyclohexyl, phenyl or benzyl, and m is an integer from 2 to 4.

6. A crystalline complex compound according to claim 1, wherein $R_1$, $R_2$, $R_4$ and $R_5$ are hydrogen, and m is 2.

7. A crystalline complex compound according to claim 1, wherein $R_{10}$ is $C_1C_4$alkyl.

8. A crystalline complex compound according to claim 1, wherein $R_1$, $R_2$, $R_4$ and $R_5$ are hydrogen, $R_3$ is hydrogen, $C_1$–$C_4$alkyl, phenyl or chloro,
$R_{10}$ is $C_1$–$C_4$alkyl, and
m is 2.

9. A coating composition comprising
   a) an organic film-forming binder, and
   b) as corrosion inhibitor, at least one crystalline complex compound of formula I according to claim 1.

10. A coating composition according to claim 9, wherein the coating composition is a paint system.

11. A coating composition according to claim 9, wherein the coating composition is an aqueous paint system.

12. A coating composition according to claim 9, wherein component a) is selected from the group consisting of an epoxy resin, a polyurethane resin, a polyester resin, an acrylic resin, an acrylic copolymer resin, a polyvinyl resin, a phenolic resin, an alkyd resin, or a mixture of such resins.

13. A coating composition according to claim 9, which additionally comprises one or more than one component selected from the group consisting of pigments, dyes, fillers, flow control agents, dispersants, thixotropic agents, adhesion promoters, antioxidants, light stabilisers and curing catalysts.

14. A coating composition according to claim 9, which contains 0.02 to 20% of component b), based on the weight of the total solids content of said coating composition.

15. A process for for the preparation of a crystalline compound of formula I as claimed in claim 1, which comprises reacting a keto-acid of formula II

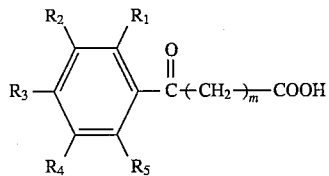
(II)

wherein the general symbols are as defined in claim 1, with a morpholine derivative of formula III

(III)

wherein $R_{10}$ is as defined in claim 1, without a solvent or in the presence of an aprotic solvent.

16. A process according to claim 15, wherein the molar ratio of the keto-acid of formula II to the morpholine derivative of formula III is 4:1 to 1:4.

17. A product obtainable by reacting a keto-acid of formula II

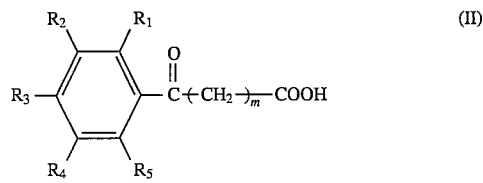
(II)

wherein the general symbols are as defined in claim 1, with a morpholine derivative of formula III

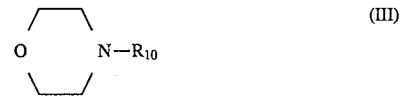
(III)

wherein $R_{10}$ is as defined in claim 1, without a solvent or in the presence of an aprotic solvent.

* * * * *